United States Patent

Yoshikawa et al.

[11] Patent Number: 5,977,172
[45] Date of Patent: Nov. 2, 1999

[54] $PGE_1$-CONTAINING-FREEZE DRIED PREPARATION AND PROCESS FOR THE PRODUCTION THEREOF

[75] Inventors: Hirofumi Yoshikawa, Kanagawa; Hideki Sasaki, Hyogo; Junzo Seki, Osaka, all of Japan

[73] Assignee: Nippon Shinyaku Co., Ltd., Kyoto, Japan

[21] Appl. No.: 09/043,203

[22] PCT Filed: Sep. 12, 1996

[86] PCT No.: PCT/JP96/02611

§ 371 Date: Mar. 12, 1998

§ 102(e) Date: Mar. 12, 1998

[87] PCT Pub. No.: WO97/09986

PCT Pub. Date: Mar. 20, 1997

[30] Foreign Application Priority Data

Sep. 13, 1995 [JP] Japan .................................. 7-235588

[51] Int. Cl.[6] ................................................ A61K 31/215
[52] U.S. Cl. ............................................................ 514/530
[58] Field of Search .............................................. 514/530

[56] References Cited

U.S. PATENT DOCUMENTS

| 4,493,847 | 1/1985 | Mizushima et al. ............... 426/317 |
| 5,091,417 | 2/1992 | Watanabe et al. ................. 514/530 |
| 5,650,172 | 7/1997 | Matsuda et al. ................... 424/489 |

FOREIGN PATENT DOCUMENTS

| 0418004 | 3/1991 | European Pat. Off. . |
| 0 556 394 A1 | 11/1991 | European Pat. Off. . |
| 59-76017 | 4/1984 | Japan . |
| 4-69340 | 3/1992 | Japan . |
| 5-43450 | 2/1993 | Japan . |

*Primary Examiner*—Kevin E. Weddington
*Attorney, Agent, or Firm*—Graham & James LLP

[57] ABSTRACT

The object of the invention is to provide a high-quality pharmaceutical preparation in the field of $PGE_1$-containing fat emulsions, which is more stable bacteriologically, thermally, and against aging than any preparation hereto fore available.

The invention, thus, relates to a $PGE_1$-containing lyophilized composition derived from a fat emulsion comprising $PGE_1$, an oil component, an emulsifier, and water having a pH controlled within the neutral region. Stated differently, the invention relates to a $PGE_1$-containing lyophilized composition characterized by comprising $PGE_1$, an oil component, an emulsifier and designed to give a fat emulsion having a pH within the neutral region upon reconstitution with distilled water of pH 7.0.

33 Claims, No Drawings

PGE$_1$-CONTAINING-FREEZE DRIED PREPARATION AND PROCESS FOR THE PRODUCTION THEREOF

TECHNICAL FIELD

The present invention relates to a lyophilized composition containing prostaglandin E$_1$ (hereinafter referred to as PGE$_1$).

BACKGROUND ART

PGE$_1$, a substance having potent vasodilative and platelet aggregation inhibitory activities, is known to be a drug useful for the treatment of certain diseases such as chronic obstructive arterial diseases [thromboarteritis obliterans (TAO), arteriosclerosis obliterans (ASO)]. Nonetheless, because PGE$_1$ is inactivated rapidly in the pulmonary circulation, continuous arterial therapy which calls for an extraordinary skill, intravenous drip injection, or massive administration has been attempted clinically but these therapeutic modalities unavoidably entail adverse reactions such as vascular pain, venotitis, and systemic hypotension.

Recently, for overcoming the above disadvantage of PGE$_1$ and exploiting the outstanding efficacy of the drug, many explorations have been made for formulating PGE$_1$ into fat emulsions (Japanese Kokai Tokkyo Koho S58-222014, Kokai Tokkyo Koho H4-69340, Kokai Tokkyo Koho H4-338333, Kokai Tokkyo Koho H4-338334, Kokai Tokkyo Koho H4-338335, etc.). Actually, the PGE$_1$ fat emulsion-described in Japanese Kokai Tokkyo Koho S58-222014 is commercially available today.

The above commercial PGE$_1$ fat emulsion is a useful PGE$_1$ preparation, for PGE$_1$ entrapped in emulsion vehicles is inactivated in the lungs only to a limited extent and this advantage coupled with the vascular lesion-targeting effect of the emulsion due to the characteristic distribution of its fine vesicles in the body produces a potent and lasting vasodilative effect at a low dose, not to speak of a reduced risk for local ADRs, for example mitigated irritancy. It is reported that this fat emulsion contains approximately 20% of decomposition products of PGE$_1$ even immediately following its manufacture and that the PGE$_1$ content declines at a rate of about 2.5% per month even when stored at 5° C. [Kazuo Mizuguchi et al., The Clinical Report, 26, 1647–1653 (1992)], thus being not impeccable in quality and stability.

As a means for insuring a sufficient stability of PGE$_1$ in a fat emulsion, lyophilization of such a PGE$_1$-containing fat emulsion was contemplated and actually much study has been undertaken for implementing a lyophilized fat emulsion (PCT WO92/07552, Japanese Kokai Tokkyo Koho H5-43450, Japanese Kokai Tokkyo Koho H6-157294, etc.). However, none of the efforts have borne fruit.

Meanwhile, each drug has a definite pH range in which it is stable and barring an extraordinary circumstance, pharmaceutical products are conventionally formulated within the pH range in which the active substance is stable for insuring a reasonable shelf-life. In the case of PGE$_1$, it is known to be stable in the weakly acidic region (Pharmaceutical Research, Vol. 5, No. 8, 482–487 (1988); Pharmaceutical Research, Vol. 6, No. 3, 210–215 (1989)), and the above-mentioned fat emulsion available on the market has also been adjusted to a weakly acidic region (pH 4.5–6.0).

DISCLOSURE OF THE INVENTION

The present invention has for its object to provide a pharmaceutical product in the field of PGE$_1$-containing fat emulsions, which is of higher quality and more stable bacteriologically, thermally, and against aging.

After an intensive research endeavor, the inventors of the present invention made a departure from the convention by adjusting the pH of a PGE$_1$-containing fat emulsion to the neutral region of pH, not to the pH range in which PGE$_1$ is known to be stable, and lyophilizing the fat emulsion and found fortunately that a pharmaceutical product meeting the above object could result from the new approach. The present invention has been developed on the basis of the above finding.

The present invention, therefore, is directed to a PGE$_1$-containing lyophilized composition derived from a fat emulsion comprising PGE$_1$, an oil component, an emulsifier, and water and having a pH controlled within the neutral region. When this PGE$_1$-containing lyophilizate is reconstituted with water at pH 7.0 (e.g. distilled water, deionized water), the reconstituted emulsion shows substantially the same pH as that before lyophilization, although a minor alteration of pH takes place. Thus, stated differently, the present invention is directed to a PGE$_1$-containing lyophilized composition comprising PGE$_1$, an oil component, and an emulsifier and showing a pH value within the neutral region upon reconstitution with water of pH 7.0.

The present invention is now described in detail.

The oil component for use in the present invention may for example be a vegetable oil, an animal oil, a neutral fat (a mono-, di-, or triglyceride), a synthetic oil or fat, or a sterol derivative. Specifically, the vegetable oil includes but is not limited to soybean oil, cottonseed oil, rapeseed oil, sesame oil, corn oil, peanut oil, and sufflower oil. The animal oil includes but is not limited to fish oil, and the neutral fat includes but is not limited to triolein, trilinolein, tripalmitin, tristearin, trimyristin, and triarakidonin. As an example of the synthetic fat, azone can be mentioned. The sterol derivative includes but is not limited to cholesteryl oleate, cholesteryl linolate, cholesteryl myristate, cholesteryl palmitate, and cholesteryl arachidate. Those substances may be used in combination. The preferred oil component includes triglycerides and vegetable oils predominantly composed of such triglycerides. For all practical purposes, soybean oil is preferred and highly purified soybean oil is particularly useful.

The optimal proportion of said oil component in the fat emulsion before lyophilization and that after reconstitution are dependent on its kind as well as on the other component substances contained but may judiciously be in the range of 0.1–30 w/v %, preferably 1–20 w/v %.

Referring to the emulsifier for use in the present invention, there is no particular limitation on its kind only if it can be used in the manufacture of pharmaceutical products. Thus, for example, a phospholipid or a nonionic surfactant can be mentioned. The phospholipid specifically includes but is not limited to phosphatidylcholine, phosphatidylethanolamine, phosphatidylinositol, phosphatidylserine, sphingomyelin, and lecithin. Hydrogenated phospholipids can also be used likewise. The nonionic surfactant includes but is not limited to polyalkylene glycols (e.g. polyethylene glycol with an average molecular weight of 1000–10000, preferably 4000–6000), polyoxyalkylene copolymers (e.g. polyoxyethylene-polyoxypropylene copolymer with an average molecular weight of 1000–20000, preferably 6000–10000), hydrogenated castor oil polyoxyalkylene derivatives (e.g. hydrogenated castor oil polyoxyethylene (20) ether, (40) ether, and (100) ether), and castor oil polyoxyalkylene derivatives (e.g. castor oil polyoxyethylene (20) ether, (40) ether, and (100) ether). Those emulsifiers can be used in a suitable combination. The preferred emulsifier includes egg yolk phosphatidylcholine, egg yolk lecithin, and soybean lecithin. For practical purposes, egg yolk lecithin and soybean lecithin are preferred. The object of the invention can be well accomplished by using a commercial phospholipid.

The proportion of the emulsifier in the fat emulsion before lyophilization and that after reconstitution are dependent on the type of emulsifier used and other components of the emulsion but it may suitably be within the range of 0.01–30 w/v %, preferably 0.1–20 w/v %.

The weight ratio of the oil component to the emulsifier (oil component/emulsifier ratio) is suitably within the range of 0.1–20, preferably 0.4–6.0, and more preferably 0.8–1.2 (particularly 1). A formulation with the above-mentioned ratio in the neighborhood of 1 provides a fat emulsion having a mean particle (vesicle) diameter of not over 70 nm, which provides a very satisfactory DDS (drug delivery system) effect, and, in addition, can be sterilized by filtration.

Regardless of the volume of a reconstitution solvent used, the above ratio after reconstitution is substantially unchanged from the ratio prior to lyophilization.

Water in the context of the invention discharges the function of a vehicle for emulsion vesicles or an agent for assuring the morphological integrity of the fat emulsion. Generally, such water may be water for injection (distilled water for injection).

The outstanding feature of the fat emulsion of the invention prior to lyophilization is that its pH has been adjusted to the neutral region in order to insurean improved stability of $PGE_1$ in the lyophilized composition. The term "neutral region" is used herein to mean a pH range in the neighborhood of pH 7 which is generally acknowledged to be neutral, and specifically mean the range of pH 6.5–7.5, preferably pH 6.7–7.3. This pH adjustment can be made using any pH control agent that is generally used in pharmaceutical products. The pH control agent, thus, includes inorganic acids, inorganic bases, organic acids, organic bases, and buffers. More specifically, hydrochloric acid, sulfuric acid, phosphoric acid, boric acid, citric acid, succinic acid, acetic acid, sodium hydroxide, potassium hydroxide, potassium hydrogencarbonate, sodium carbonate, triethanolamine, phosphate buffer, etc. can be mentioned. However, depending upon the kinds of oil component and emulsifier used, a fat emulsion forms in the neutral region even in the absence of a pH control agent and the pH adjustment is not required in such cases, of course.

The pH of the emulsion available upon reconstitution of the lyophilized composition of the invention with neutral water, as determined immediately following reconstitution, is substantially identical to the pH of the fat emulsion prior to lyophilization, although a minor alteration may have occurred, thus being still within the neutral region of pH, that is to say pH 6.5–7.5 or pH 6.7–7.3.

$PGE_1$ is the active component of the pharmaceutical composition of the present invention. Although the concentration of $PGE_1$ in the fat emulsion before lyophilization and that after reconstitution should vary with different formulations of the fat emulsion and different uses for the product, the range of 0.1–500 μg/ml is appropriate and the range of 1–100μg/ml is still more preferred.

In the practice of the invention, an excipient (an auxiliary lyophilizing agent) can be added for protecting the cake of the lyophilizate and other purposes. The excipient may for example be a saccharide, an amino acid, or an inorganic salt. The saccharide includes monosaccharides, disaccharides, polysaccharides, and sugar alcohols. Specifically, glucose and fructose can be mentioned as typical monosaccharides; maltose, lactose, sucrose, and trehalose as typical disaccharides; dextran, starch, and maltotriose as typical polysaccharides; and mannitol, sorbitol, and glycerol as typical sugar alcohols. Among them, monosaccharides and disaccharides are preferred, and maltose is particularly preferred. When maltose is added, the lyophilizate can be restored to a fat emulsion having a mean vesicle diameter and vesicle size distribution closely approximating those of the emulsion prior to lyophilization. The amino acid may for example be glycine and the inorganic salt may for example be sodium chloride or potassium chloride. Those excipients can be used not only independently but in a suitable combination. Incidentally, an inorganic salt, particularly sodium chloride, inhibits aggregation and coalescence of fat emulsion vesicles.

The saccharide content of the fat emulsion prior to lyophilization and that after reconstitution are dependent on the kinds of saccharide and other components used but is judiciously within the range of 1–30 w/v %, preferably 3–20 w/v %. The amino acid content of the fat emulsion prior to lyophilization and that after reconstitution should vary with different kinds of amino acid and other components used but may judiciously be within the range of 1–30 w/v %, preferably 3–20 w/v %. The inorganic salt content of the fat emulsion prior to lyophilization and that after reconstitution should also vary with different kinds of inorganic salt and other components but may judiciously be within the range of 0.5–5 w/v %.

In the present invention, an auxiliary emulsifier or an emulsion stabilizer can be added where necessary. The auxiliary emulsifier or emulsion stabilizer mentioned above includes straight-chain or branched $C_{6-22}$ saturated or unsaturated fatty acids, e.g. stearic acid, oleic acid, linoleic acid, palmitic acid, linolenic acid, myristic acid, etc. and their salts (e.g. alkali metal salts, e.g. sodium salts, potassium salts, etc. and alkaline earth metal salts, (e.g. calcium salts); primary or secondary aliphatic $C_{2-22}$ amines, e.g. ethanolamine, propylamine, octylamine, stearylamine, oleylamine, etc., basic amino acids such as lysine, histidine, ornithine, arginine, etc., sterols such as cholesterol, cholestanol, etc., phosphatidic acid, and charged substances such as gangliosides, steary lamine, and so on. Those substances can be used not only independently or in a suitable combination.

The amounts of such additives in the fat emulsion prior to lyophilization or after reconstitution are dependent on the objectives of addition but are generally not larger than 1 w/v %, preferably not larger than 2 w/v %. It should be understood that even without use of those additives, the object of the present invention can be well accomplished.

Where necessary, such additives as an antioxidant, antiseptic, isotonizing agent, buffer, stabilizer, etc., which may be contained in pharmaceutical products in general, as well as auxiliary agents, nutrients, etc. can also be added. Specifically, benzoic acid, ascorbic acid, tocopherol, etc. can be mentioned. Those substances can be generally added in suitable quantities and sufficient effects can be expected at addition levels not over 10 w/v %.

The fat emulsion of the present invention, whether before lyophilization or after reconstitution, comprises emulsion vesicles (particles) predominantly composed of the oil component and emulsifier, and it is assumed that $PGE_1$ exists as entrapped in those vesicles. The vesicles are very fine with a mean particle diameter of 5–500 nm. Preferred, however, are vesicles with a mean particle diameter not in excess of 250 nm. The more preferred mean particle diameter is 5–70 nm, and vesicles with a mean particle diameter of 5–50 nm are particularly preferred. Emulsion vesicles with a mean particle diameter in the range of 5–70 nm can pass a 0.2 μm membrane filter nearly 100% so that sufficient sterility can be assured by filtration without resort to autoclaving. Membrane filtration yields an emulsion with a reduced impurity content, for the formation of decomposition products associated with heating can be circumvented. However, since membrane filtration is not as effective as autoclaving for ensuring sterility, there may be an apprehension of greater chances for growth of microorganisms. However, growth of microorganisms can be well inhibited by lyophilization.

The lyophilized composition of the present invention can be provided by freeze-drying a fat emulsion comprising $PGE_1$, and an oil component, an emulsifier, and water and having a pH controlled within the neutral region in accordance with the conventional lyophilization protocol. The oil component, emulsifier, water, neutral region, and fat emulsion mentioned above are respectively as defined hereinbefore.

A process for producing a lyophilized composition according to the present invention is now described in detail.

In the first place, a $PGE_1$-containing fat emulsion, not freeze-dried as yet, is provided. This fat emulsion can be prepared as follows. Thus, suitable amounts of $PGE_1$ and the emulsifier as well as said additives are added to a predetermined amount of the oil component according to the above-mentioned formulation and the mixture is homogenized, typically with warming. To the resulting homogenate is added a suitable amount of water and the whole mixture is emulsified using an ordinary homomixer or homogenizer, a sonic homogenizer, Microfluidizer™, Nanomizer™, Ultimizer™, or a Manton-Gaulin type high-pressure homogenizer until an emulsion having a mean particle diameter within the above-mentioned range has been obtained. Depending on production needs, components other than said $PGE_1$, oil component, emulsifier, auxiliary emulsifier, and emulsion stabilizer (for example, the excipient and pH control agent) can be added after formation of a fat emulsion. The pH adjustment can be carried out after addition of all the components other than the pH control agent, whether before emulsification or after emulsification.

The lyophilized composition of the invention can be simply obtained by freeze-drying the above fat emulsion in the per se known manner. Thus, the conventional lyophilization technology can be used for this procedure. For example, the fat emulsion is first sterilized and distributed in aliquots into vials. The vials are then subjected to preliminary freeze-drying at about −40—−20° C. for about 2 hours, then to primary drying under reduced pressure at about 0–10° C., and further to secondary drying under reduced pressure at about 15–25° C. The vials are generally purged with nitrogen gas and then stoppered to provide lyophilized products.

When a suitable solvent (reconstitution medium) is added, the lyophilizate of the invention redissolves quite readily to give a fat emulsion approximating the emulsion prior to lyophilization. The reconstitution medium may for example be water for injection, physiological saline, or an infusion for general use. The quantity of the reconstitution medium varies with different uses and is not particularly limited. However, it may judiciously be 0.5–2 times the volume of the emulsion prior to lyophilization or not larger than 500 ml/vial.

The lyophilized composition thus reconstituted with water for injection or the like can be administered parenterally, for example by injection. Particularly preferred is intravenous administration. The administration method varies with therapeutic objects but includes one-shot administration once a day, administration in 3 divided doses daily, or continuous intravenous drip injection, for instance.

The lyophilized composition of the present invention can be used in any of the indications for $PGE_1$. For example, it can be used as a therapeutic drug for chronic obstructive arterial diseases, progressive systemic scleroderma, systemic lupus erythematosus, diabetes, and vibration disease.

BEST MODE FOR CARRYING OUT THE INVENTION

The following examples and test examples are intended to illustrate the present invention in further detail and should by no means be construed as defining the scope of the invention.

EXAMPLE 1

At a temperature of about 40° C., 10 g of purified soybean oil, 1.8 g of purified egg yolk lecithin, and 0.5 mg of $PGE_1$ were admixed, and after addition of about 80 ml of a 10% aqueous solution of maltose, the mixture was agitated in a homogenizer to prepare a crude dispersion. This crude dispersion was further diluted with a 10% aqueous solution of maltose and adjusted to pH 7.0 with sodium hydroxide to provide 100 ml. Using a Manton Gaulin type homogenizer, this crude dispersion was emulsified under ice-cooling and pressurization using a total pressure of 500 kg/cm$^3$ in 10 passes to provide a homogenous $PGE_1$-containing fat emulsion. The mean particle diameter of this emulsion as measured with a light-scattering photometer (DLS-700, Otsuka Densi; the same applies hereinafter) was 203 nm. The emulsion obtained above was dispensed in 1 ml aliquots into 1 ml vials and lyophilized to provide a lyophilized composition of the present invention. This lyophilization was carried out as follows. Using a Kyowa freeze-dryer (RL-20MB, manufactured by Kyowa Vacuum), the emulsion was serially subjected to 2-hour preliminary freeze-drying at −40° C., 10-hour primary drying under reduced pressure at 0° C., and 5-hour secondary drying under reduced pressure at 25° C. The resulting lyophilizate was very satisfactory in condition with no evidence at all of chipping, cracking, shrinkage, and other defects. When the lyophilized composition was redissolved (reconstituted into 1 ml fat emulsion) in water for injection, dissolution went to completion very rapidly and the original fat emulsion was almost faithfully reproduced with little alterations in the mean particle diameter and particle size distribution. Incidentally, the mean particle diameter of the reconstituted emulsion was 210 nm. The pH of this fat emulsion immediately after reconstitution to 1 ml with distilled water of pH 7.0 was pH 6.9.

EXAMPLE 2

Except that 0.24 g of oleic acid was added, the procedure of Example 1 was repeated to prepare a fat emulsion with a mean particle diameter of 195 nm and using this emulsion a lyophilized composition of the invention was obtained. The lyophilizate was very satisfactory in condition with no evidence at all of chipping, cracking, shrinkage and other defects. When this lyophilizate was redissolved in water for injection (reconstituted to 1 ml fat emulsion), dissolution went to completion very rapidly and the original fat emulsion prior to lyophilization was almost faithly reproduced with no appreciable alterations in the mean particle diameter and particle size distribution. Incidentally, the mean particle diameter of the reconstituted emulsion was 201 nm. The pH of this fat emulsion immediately after reconstitution to 1 ml with distilled water of pH 7.0 was pH 6.7.

EXAMPLE 3

At a temperature of about 40° C., 5 g of purified soybean oil, 5 g of purified egg yolk lecithin, and 0.5 mg of $PGE_1$ were admixed, and after addition of about 80 ml of a 10% aqueous solution of maltose, the mixture was agitated in a homogenizer to prepare a crude dispersion. This crude dispersion was further diluted with a 10% aqueous solution of maltose and adjusted to pH 7.0 with sodium hydroxide to provide 100 ml. This crude dispersion was pressure-emulsified with a Nanomizer (LA-31, Nanomizer Co.) under ice-cooling to give a homogeneous fat emulsion containing finely divided particles of $PGE_1$. The mean particle diameter of this emulsion as measured with a light-scattering photometer was 33 nm. This emulsion was filtered through a 0.2 $\mu$m membrane filter and dispensed in 1 ml aliquots into 1 ml vials, which were then lyophilized to provide a lyophilized composition of the present invention. Using a Kyowa freeze-dryer (RL-20MB, manufactured by Kyowa Vacuum), the emulsion was serially subjected to 2-hour freeze-drying at −40° C., 10-hour primary drying under reduced pressure at 0° C., and 5-hour secondary drying under reduced pressure at 25° C. The lyophilizate was very satisfactory in condition with no evidence at all of chipping, cracking, shrinkage, and other defects. When the lyophilized composition was redissolved (reconstituted into 1 ml fat emulsion) in water for injection, dissolution went to completion very rapidly and the original fat emulsion was almost faithfully reproduced with little alterations in the mean particle diameter and particle size distribution. Incidentally, the mean particle diameter of the reconstituted emulsion was 34 nm. The pH of this fat emulsion immediately after reconstitution to 1 ml with distilled water of pH 7.0 was pH 7.0.

EXAMPLE 4

Except that 0.24 g of oleic acid was added, the procedure of Example 3 was otherwise repeated to prepare a fat emulsion with a mean particle diameter of 38 nm and using this emulsion a lyophilized composition of the invention was obtained. The lyophilizate was very satisfactory in condition with no evidence at all of chipping, cracking, shrinkage and other defects. When this lyophilizate was redissolved in water for injection (reconstituted to 1 ml fat emulsion), dissolution went to completion very rapidly and the original fat emulsion prior to lyophilization was almost faithly reproduced with no appreciable alterations in the mean particle diameter and particle size distribution. Incidentally, the mean particle diameter of the reconstituted emulsion was 40 nm. The pH of this fat emulsion immediately after reconstitution to 1 ml with distilled water of pH 7.0 was pH 6.9.

EXAMPLE 5

Using 3 g of purified egg yolk lecithin, the procedure of Example 3 was otherwise repeated to give a fat emulsion with a mean particle diameter of 42 nm and using this emulsion a lyophilized composition of the invention was obtained. The lyophilizate was very satisfactory in condition with no evidence at all of chipping, cracking, shrinkage and other defects. When this lyophilizate was redissolved in water for injection (reconstituted to 1 ml fat emulsion), dissolution went to completion very rapidly and the original fat emulsion prior to lyophilization was almost faithly reproduced with no appreciable alterations in the mean particle diameter and particle size distribution. Incidentally, the mean particle diameter of the reconstituted emulsion was 41 nm. The pH of this fat emulsion immediately after reconstitution to 1 ml with distilled water of pH 7.0 was pH 6.8.

EXAMPLE 6

Using soybean lecithin in lieu of purified egg yolk lecithin, the procedure of Example 3 was otherwise repeated to give a fat emulsion with a mean particle diameter of 43 nm and using this emulsion a lyophilized composition of the invention was obtained. The lyophilizate was very satisfactory in condition with no evidence at all of chipping, cracking, shrinkage and other defects. When this lyophilizate was redissolved in water for injection (reconstituted to 1 ml fat emulsion), dissolution went to completion very rapidly and the original fat emulsion prior to lyophilization was almost faithly reproduced with no appreciable alterations in the mean particle diameter and particle size distribution. Incidentally, the mean particle diameter of the reconstituted emulsion was 45 nm. The pH of this fat emulsion immediately after reconstitution to 1 ml with distilled water of pH 7.0 was pH 7.3.

EXAMPLE 7

Except that the pH was adjusted to 6.5, the procedure of Example 3 was otherwise repeated to give a fat emulsion with a mean particle diameter of 35 nm and using this emulsion a lyophilized composition of the invention was obtained. The lyophilizate was very satisfactory in condition with no evidence at all of chipping, cracking, shrinkage and other defects. When this lyophilizate was redissolved in water for injection (reconstituted to 1 ml fat emulsion), dissolution went to completion very rapidly and the original fat emulsion prior to lyophilization was almost faithly reproduced with no appreciable alterations in the mean particle diameter and particle size distribution. Incidentally, the mean particle diameter of the reconstituted emulsion was 35 nm. The pH of this fat emulsion immediately after reconstitution to 1 ml with distilled water of pH 7.0 was pH 6.5.

EXAMPLE 8

Except that the pH was adjusted to 7.5, the procedure of Example 3 was otherwise repeated to give a fat emulsion with a mean particle diameter of 34 nm and using this emulsion a lyophilized composition of the invention was obtained. The lyophilizate was very satisfactory in condition with no evidence at all of chipping, cracking, shrinkage and other defects. When this lyophilizate was redissolved in water for injection (reconstituted to 1 ml fat emulsion), dissolution went to completion very rapidly and the original fat emulsion prior to lyophilization was almost faithly reproduced with no appreciable alterations in the mean particle diameter and particle size distribution. Incidentally, the mean particle diameter of the reconstituted emulsion was 36 nm. The pH of this fat emulsion immediately after reconstitution to 1 ml with distilled water of pH 7.0 was pH 7.4.

COMPARATIVE EXAMPLE 1

Except that the pH was adjusted to 6.0, the procedure of Example 3 was otherwise repeated to give a fat emulsion with a mean particle diameter of 35 nm and using this emulsion a lyophilized composition was obtained. The pH of this fat emulsion immediately after reconstitution to 1 ml with distilled water of pH 7.0 was pH 6.1.

COMPARATIVE EXAMPLE 2

Except that the pH was adjusted to 5.0, the procedure of Example 3 was otherwise repeated to give a fat emulsion with a mean particle diameter of 34 nm and using this emulsion a lyophilized composition was obtained. The pH of this fat emulsion immediately after reconstitution to 1 ml with distilled water of pH 7.0 was pH 5.1.

COMPARATIVE EXAMPLE 3

Except that the pH was adjusted to 8.5, the procedure of Example 3 was otherwise repeated to give a fat emulsion with a mean particle diameter of 36 nm and using this emulsion a lyophilized composition was obtained. The pH of this fat emulsion immediately after reconstitution to 1 ml with distilled water of pH 7.0 was pH 8.4.

TEST EXAMPLE 1

Storage Stability Test (1)

Using the lyophilized compositions obtained in Examples 3, 7, and 8 and in Comparative Examples 1, 2, and 3, the percent residues of $PGE_1$ after one month of storage at 40° C. were investigated. The results are shown in Table 1. The percent $PGE_1$ residue was in variably determined after reconstitution (reconstituted to 1 ml fat emulsion) with water for injection immediately following the specified storage period.

TABLE 1

| Sample | | pH | Residual $PGE_1$ (%) |
|---|---|---|---|
| Comparative Example 2 | Weakly acidic | 5.0 | 80 |
| Comparative Example 1 | | 6.0 | 82 |
| Example 7 | | 6.5 | 93 |
| Example 3 | Neutral | 7.0 | 95 |
| Example 8 | | 7.5 | 92 |
| Comparative Example 3 | Weakly basic | 8.5 | 75 |

It is apparent from Table 1 that compared with $PGE_1$ in the lyophilized compositions obtained after adjustment of the fat emulsion to the weakly acidic region (pH 5.0 or 6.0) or weakly alkaline region (pH 8.5) prior to freeze-drying, the stability of $PGE_1$ in the lyophilized compositions obtained after adjustment of the fat emulsion to the neutral region (pH 6.5–7.5) prior to freeze-drying was remarkably higher.

TEST EXAMPLE 2

Storage Stability Test (2)

Using the lyophilized composition of the invention as obtained in Example 3 and a commercial fat emulsion (registered trademark: Liple), the percent residues of $PGE_1$ after one week of storage at 40° C. were investigated. The results are shown in Table 2. As to the percent residue of $PGE_1$ in the lyophilized composition of Example 3, the composition reconstituted with water for injection (reconstituted to 1 ml fat emulsion) after said storage period was used as the sample.

TABLE 2

| Sample | Residual $PGE_1$ (%) |
|---|---|
| Example 3 (lyophilized) | 100 |
| Commercial fat emulsion (liquid) | 70 |

It will be apparent from Table 2 that the stability of $PGE_1$ in the lyophilized composition according to Example 3 of the present invention was remarkably higher than the stability of $PGE_1$ in the commercial fat emulsion.

EFFECTS OF THE INVENTION

The $PGE_1$-containing lyophilized composition of the present invention is remarkably superior, in the stability of $PGE_1$, to the $PGE_1$-containing lyophilized composition derived from a fat emulsion not adjusted to the neutral region of pH prior to lyophilization. Moreover, because the fat emulsion is adjusted to the neutral region of pH prior to lyophilization in the present invention, the increase in the free fatty acid content of the fat emulsion due to hydrolysis is suppressed and the stability (degree of maintenance of particle diameter and particle size distribution) of emulsion vesicles is also high.

Furthermore, the lyophilized composition of the present invention as derived from a fat emulsion having a mean particle diameter of 5–70 nm is remarkably more stable as compared with the commercial liquid type fat emulsion, for it does not contain water (inhibition of hydrolysis of $PGE_1$) and that it has been sterilized by filtration (prevention of the unwanted thermal degradation of $PGE_1$ which is inevitable with autoclaving). Moreover, the composition has little impurity.

In accordance with the present invention, there can thus be provided a $PGE_1$-containing medicinal preparation of high quality.

What is claimed is:

1. A $PGE_1$-containing lyophilized composition derived from a fat emulsion comprising prostaglandin $E_1$ ($PGE_1$), an oil component, an emulsifier, and water and having a pH controlled within the neutral region prior to lyophilization.

2. A $PGE_1$-containing lyophilized composition according to claim 1 as derived from the fat emulsion defined in claim 1, said fat emulsion containing said oil component in a proportion of 0.1–30 w/v % and said emulsifier in a proportion of 0.01–30 w/v %.

3. A $PGE_1$-containing lyophilized composition according to claim 1 as derived from the fat emulsion defined in claim 1, the average particle diameter of vesicles in said fat emulsion being within a range of 5–70 nm.

4. A $PGE_1$-containing lyophilized composition according to claim 3 as derived from the fat emulsion defined in claim 3 and containing said oil component and said emulsifier in a weight ratio (oil/emulsifier ratio) of 0.8–1.2.

5. A $PGE_1$-containing lyophilized composition according to claim 1 as derived from the fat emulsion defined in claim 1 wherein said oil component is a vegetable oil or a triglyceride and said emulsifier is a phospholipid or a nonionic surfactant.

6. A $PGE_1$-containing lyophilized composition according to claim 5 as derived from the fat emulsion defined in claim 5 wherein the vegetable oil is soybean oil and the phospholipid is egg yolk lecithin.

7. A $PGE_1$-containing lyophilized composition according to claim 1 as derived from the fat emulsion defined in claim 1 and having a pH of 6.5–7.5.

8. A $PGE_1$-containing lyophilized composition according to claim 1 as derived from the fat emulsion defined in claim 1 and further comprising a saccharide.

9. A $PGE_1$-containing lyophilized composition according to claim 8 as derived from the fat emulsion defined in claim 8, the saccharide content of said fat emulsion being within a range of 1–30 w/v %.

10. A $PGE_1$-containing lyophilized composition according to claim 8 as derived from the fat emulsion defined in claim 8 wherein said saccharide is maltose.

11. A $PGE_1$-containing lyophilized composition according to claim 1 as derived from the fat emulsion defined in claim 1 and further comprising a fatty acid and/or cholesterol.

12. A $PGE_1$-containing lyophilized composition characterized by comprising prostaglandin $E_1$ ($PGE_1$), an oil component, and an emulsifier and giving a pH within the neutral region immediately after reconstitution with water of pH 7.0.

13. A $PGE_1$-containing lyophilized composition according to claim 12 which, as determined immediately after reconstitution, contains said oil component in a proportion of 0.1–30 w/v % and said emulsifier in a proportion of 0.01–30 w/v %.

14. A $PGE_1$-containing lyophilized composition according to claim 12 which, immediately after reconstitution, shows a mean particle diameter of fat emulsion vesicles within a range of 5–70 nm.

15. A $PGE_1$-containing lyophilized composition according to claim 14 which, as determined immediately after reconstitution, contains said oil component and said emulsifier in a weight ratio (oil/emulsifier ratio) of 0.8–1.2.

16. A $PGE_1$-containing lyophilized composition according to claim 12 wherein the oil component is a vegetable oil or a triglyceride and the emulsifier is a phospholipid or a nonionic surfactant.

17. A $PGE_1$-containing lyophilized composition according to claim 16 wherein the vegetable oil is soybean oil and the phospholipid is egg yolk lecithin.

18. A $PGE_1$-containing lyophilized composition according to claim 12 which gives a pH of 6.5–7.5 immediately after reconstitution with water of pH 7.0.

19. A $PGE_1$-containing lyophilized composition according to claim 12 which further comprises a saccharide.

20. A $PGE_1$-containing lyophilized composition according to claim 19, the saccharide content of which is 1–30 w/v % after reconstitution.

21. A $PGE_1$-containing lyophilized composition according to claim 19 wherein the saccharide is maltose.

22. A $PGE_1$-containing lyophilized composition according to claim 12 which further comprises a fatty acid and/or cholesterol.

23. A process for producing a $PGE_1$-containing lyophilized composition characterized in that a fat emulsion comprising prostaglandin $E_1$ ($PGE_1$), an oil component, an emulsifier, and water and having a pH controlled within the neutral region is freeze-dried.

24. A process for producing a $PGE_1$-containing lyophilized composition as claimed in claim 23 further characterized in that the fat emulsion defined in claim 23 and containing said oil component in a proportion of 0.1–30 w/v % and said emulsifier in a proportion of 0.01–30 w/v % is freeze-dried.

25. A process for producing a $PGE_1$-containing lyophilized composition as claimed in claim 23 further characterized in that the fat emulsion defined in claim 23 and having a mean particle diameter of 5–70 nm is freeze-dried.

26. A process for producing a $PGE_1$-containing lyophilized composition as claimed in claim 25 further characterized in that the fat emulsion defined in claim 25 and containing said oil component and emulsifier in a weight ratio (oil/emulsifier) of 0.8–1.2 is freeze-dried.

27. A process for producing a $PGE_1$-containing lyophilized composition as claimed in claim 23 further characterized in that the fat emulsion defined in claim 23 and containing a vegetable oil or a triglyceride as said oil component and a phospholipid or a nonionic surfactant as said emulsifier is freeze-dried.

28. A process for producing a $PGE_1$-containing lyophilized composition as claimed in claim 27 further characterized in that the fat emulsion defined in claim 27 and containing soybean oil as said vegetable oil and egg yolk lecithin as said phospholipid is freeze-dried.

29. A process for producing a $PGE_1$-containing lyophilized composition as claimed in claim 23 further characterized in that the fat emulsion defined in claim 23 and having a pH controlled within a range of 6.5–7.5 is freeze-dried.

30. A process for producing a $PGE_1$-containing lyophilized composition as claimed in claim 23 further characterized in that the fat emulsion defined in claim 23 and further comprising a saccharide is freeze-dried.

31. A process for producing a $PGE_1$-containing lyophilized composition as claimed in claim 30 further characterized in that the fat emulsion defined in claim 30 and having a saccharide content of 1–30 w/v % is freeze-dried.

32. A process for producing a $PGE_1$-containing lyophilized composition as claimed in claim 30 further characterized in that the fat emulsion defined in claim 30 and containing maltose as said saccharide is freeze-dried.

33. A process for producing a $PGE_1$-containing lyophilized composition as claimed in claim 23 further characterized in that the fat emulsion defined in claim 23 and further comprising a fatty acid and/or cholesterol is freeze-dried.

\* \* \* \* \*